United States Patent
Hull et al.

(10) Patent No.: US 6,542,903 B2
(45) Date of Patent: **\*Apr. 1, 2003**

(54) TEXT INFLUENCED MOLECULAR INDEXING SYSTEM AND COMPUTER-IMPLEMENTED AND/OR COMPUTER-ASSISTED METHOD FOR SAME

(75) Inventors: Richard D. Hull, Orlando, FL (US); Eugene M. Fluder, Jr., Hamilton Square, NJ (US); Suresh B. Singh, Kendall Park, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/925,636

(22) Filed: Aug. 10, 2001

(65) Prior Publication Data

US 2002/0087508 A1 Jul. 4, 2002

Related U.S. Application Data

(63) Continuation of application No. 09/624,209, filed on Jul. 24, 2000, now Pat. No. 6,332,138.
(60) Provisional application No. 60/145,210, filed on Jul. 23, 1999.

(51) Int. Cl.$^7$ .............................................. G06F 17/30
(52) U.S. Cl. ........................................ 707/104.1; 707/3
(58) Field of Search .......................... 707/104.1, 1, 3, 707/5–6, 102

(56) References Cited

U.S. PATENT DOCUMENTS 5,878,373 A    3/1999   Cohen et al. ................. 702/22

FOREIGN PATENT DOCUMENTS

| EP | 0 510 634 A2 | 10/1992 | |
|---|---|---|---|
| EP | 0 829 810 A1 | 3/1998 | |
| WO | WO-00/62251 A1 | 10/2000 | ............ G06N/7/00 |

OTHER PUBLICATIONS

Xie, et al. An Efficient Protocol for Chemical Databases: Singular Value Decomposition Combined With Truncated–Newton Minimization, published on web Dec. 1, 1999, J. Chem. Inf. Comput. Science, 2000, 40, pp. 167–177.

In re Schittler and Uffer, 110 USPQ 304 (CCPA 1956).

*Primary Examiner*—Diane D. Mizrahi
(74) *Attorney, Agent, or Firm*—Irah H. Donner; Hale and Dorr LLP

(57) ABSTRACT

An extension of the vector space model for computing chemical similarity using textual and chemical descriptors is described. The method uses a chemical and/or textual description of a molecule/chemical and a decomposes a molecule/chemical descriptor matrix by a suitable technique such as singular value decomposition to create a low dimensional representation of the original descriptor space. Similarities between a user probe and the textual and/or chemical descriptors are then computed and ranked.

64 Claims, 7 Drawing Sheets

TEXT INFLUENCED MOLECULAR INDEXING SYSTEM AND COMPUTER-IMPLEMENTED AND/OR COMPUTER-ASSISTED METHOD FOR SAME

RELATED APPLICATIONS

This application is a continuation application of U.S. application Ser. No. 09/624,209, filed Jul. 24, 2000, now U.S. Pat. No. 6,332,138 which in turn claims priority to U.S. Provisional Application Serial No. 60/145,210, filed Jul. 23, 1999, both of which are incorporated herein by reference. This application is related in subject matter to co-pending U.S. patent application Ser. No. 09/546,399, filed Apr. 10, 2000 by Eugene M. Fluder et al. for "Chemical Structure Similarity Ranking System and Computer-Implemented Method For Same" and assigned to The Merck & Co., Inc, incorporated herein by reference.

DESCRIPTION

BACKGROUND OF THE INVENTION

1. Field of the Invention

The present invention generally relates to computer-based and/or computer-assisted calculation of the chemical and/or textual similarity of chemical structures, compounds, and/or molecules and, more particularly, to ranking the similarity of chemical structures, compounds, and/or molecules with regard to the chemical and/or textual description of, for example, a user's probe proposed, and/or lead compound(s).

2. Background Description

In recent years, pharmaceutical companies have developed large collections of chemical structures, compounds, or molecules. Typically, one or more employees of such a company will find that a particular structure in the collection has an interesting chemical and/or biological activity (e.g., a property that could lead to a new drug, or a new understanding of a biological phenomenon).

Similarity searches are a standard tool for drug discovery. A large portion of the effort expended in the early stages of a drug discovery project is dedicated to finding "lead" compounds (i.e., compounds which can lead the project to an eventual drug). Lead compounds are often identified by a process of screening chemical databases for compounds "similar" to a probe compound of known activity against the biological target of interest. Computational approaches to chemical database screening have become a foundation of the drug industry because the size of most commercial and proprietary collections has grown dramatically over the last decade.

Chemical similarity algorithms operate over representations of chemical structure based on various types of features called descriptors. Descriptors include the class of two dimensional representations and the class of three dimensional representations. As will be recognized by those skilled in the art, two dimensional representations include, for example, standard atom pair descriptors, standard topological torsion descriptors, standard charge pair descriptors, standard hydrophobic pair descriptors, and standard inherent descriptors of properties of the atoms themselves. By way of illustration, regarding the atom pair descriptors, for every pair of atoms in the chemical structure, a descriptor is established or built from the type of atom, some of its chemical properties, and its distance from the other atom in the pair.

Three dimensional representations include, for example, standard descriptors accounting for the geometry of the chemical structure of interest, as mentioned above. Geometry descriptors may take into account, for example, the fact that a first atom is a short distance away in three dimensions from a second atom, although the first atom may be twenty bonds away from the second atom. Topological similarity searches, especially those based on comparing lists of precomputed descriptors, are computationally very inexpensive.

The vector space model of chemical similarity involves the representation of chemical compounds as feature vectors. As will be recognized by those skilled in the art, exemplary features include substructure descriptors such as atom pairs (see Carhart, R. E.; Smith, D. H.; Venkataraghavan, R., "Atom Pairs as Molecular Features in Structure-Activity Studies: Definition and Applications", *J. Chem. Inf. Comp. Sci.* 1985, 25:64–73) and/or topological torsions (see Nilakantan, R.; Bauman, N.; Dixon, J. S; Venkataraghavan, R., "Topological Torsions: A New Molecular Descriptor for SAR Applications", *J. Chem. Inf. Comp. Sci.* 1987, 27:82–85), all incorporated herein by reference.

As seen, many strategies for representing molecules in the collection and computing similarity between them have been devised. We have recognized, however, that these searches are often more involved when the goal is to select compounds that have similar activity or properties, but not obviously similar structure. That is, we have identified a need to ascertain, from a large collection of chemical structures, compounds, or molecules, a set of diverse chemical structures, for example, that may look dissimilar from the original probe compound, but exhibit similar chemical or biological activity. We have also recognized that although algorithms using, for example, Dice-type and/or Tanimoto-type coefficients, each known to those skilled in the art, by design, yield compounds that are most similar to the probe compound, such algorithms may fail to provide compounds or chemical structures characterized by diversity relative to the probe compound.

With respect to a chemical example, if a particular compound were found to be a HIV inhibitor, we have recognized that it would be desirable to search a database of chemical compounds or compositions and identify HIV inhibitors that have the same or similar pharmacological effect as the original HIV inhibitor, but that may be structurally dissimilar to the original HIV inhibitor probe. The capability of being able to find one or more dissimilar HIV inhibitors quickly and effectively can potentially be worth billions of dollars in revenue.

We have also recognized that utilizing a probe and providing a database that includes a textual description in addition to a chemical description reveals correlations and relationships therebetween that cannot be obtained by utilizing either textual or chemical descriptors alone.

Latent Semantic Indexing and Latent Semantic Structure Indexing

The present invention, called Text Influenced Molecular Indexing (TIMI), expands upon the Latent Semantic Indexing (LSI) methodology described in U.S. Pat. No. 4,839,853 to Deerwester et al., incorporated herein by reference.

Deerwester discloses a methodology for retrieving textual data objects, in response to a user's query, principally by representing a collection of text documents as a term-document matrix for the purpose of retrieving documents from a corpus. Deerwester postulates that there is an underlying latent semantic structure in word usage data that is partially hidden or obscured by the variability of word choice. A statistical approach is utilized to estimate this latent semantic structure and uncover the latent meaning. Deerwester shows that given the partial Singular Value Decomposition (SVD) of matrix X, it is possible to compute similarities between language terms, between documents, and between a term and a document. The SVD technique is well-known in the mathematical and computational arts and has been used in many scientific and engineering applications including signal and spectral analysis. Furthermore, Deerwester computes the similarity of ad hoc queries (column vectors which do not exist in X) to both the terms and the documents in the database.

Specifically, and referring to FIG. 1, the method disclosed in Deerwester comprises the following steps. The first processing activity, as illustrated by processing block 100, is that of text processing. All the combined text is preprocessed to identify terms and possible compound noun phrases. First, phrases are found by identifying all words between (1) a precompiled list of stop words; or (2) punctuation marks; or (3) parenthetical remarks.

To obtain more stable estimates of word frequencies, all inflectional suffixes (past tense, plurals, adverbials, progressive tense, and so forth) are removed from the words. Inflectional suffixes, in contrast to derivational suffixes, are those that do not usually change the meaning of the base word. (For example, removing the "s" from "boys" does not change the meaning of the base word whereas stripping "ation" from "information" does change the meaning). Since no single set of pattern-action rules can correctly describe English language, the suffix stripper sub-program may contain an exception list.

The next step to the processing is represented by block 110. Based upon the earlier text preprocessing, a system lexicon is created. The lexicon includes both single word and noun phrases. The noun phrases provide for a richer semantic space. For example, the "information" in "information retrieval" and "information theory" have different meanings. Treating these as separate terms places each of the compounds at different places in the k-dimensional space. (for a word in radically different semantic environments, treating it as a single word tends to place the word in a meaningless place in k-dimensional space, whereas treating each of its different semantic environments separately using separate compounds yields spatial differentiation).

Compound noun phrases may be extracted using a simplified, automatic procedure. First, phrases are found using the "pseudo" parsing technique described with respect to step 100. Then all left and right branching subphrases are found. Any phrase or subphrase that occurs in more than one document is a potential compound phrase. Compound phrases may range from two to many words (e.g., "semi-insulating Fe-doped InP current blocking layer"). From these potential compound phrases, all longest-matching phrases as well as single words making up the compounds are entered into the lexicon base to obtain spatial separation.

In the illustrative embodiment, all inflectionally stripped single words occurring in more than one document and that are not on the list of most frequently used words in English (such as "the", "and") are also included in the system lexicon. Typically, the exclusion list comprises about 150 common words.

From the list of lexicon terms, the Term-by-Document matrix is created, as depicted by processing block 120. In one exemplary situation, the matrix contained 7100 terms and 728 documents representing 480 groups.

The next step is to perform the singular value decomposition on the Term-by-Document matrix, as depicted by processing block 130. This analysis is only effected once (or each time there is a significant update in the storage files).

The last step in processing the documents prior to a user query is depicted by block 140. In order to relate a selected document to the group responsible for that document, an organizational database is constructed. This latter database may contain, for instance, the group manager's name and the manager's mail address.

The user query processing activity is depicted in FIG. 2. The first step, as represented by processing block 200, is to preprocess the query in the same way as the original documents.

As then depicted by block 210 the longest matching compound phrases as well as single words not part of compound phrases are extracted from the query. For each query term also contained in the system lexicon, the k-dimensional vector is located. The query vector is the weighted vector average of the k-dimensional vectors. Processing block 220 depicts the generation step for the query vector.

The next step in the query processing is depicted by processing block 230. In order that the best matching document is located, the query vector is compared to all documents in the space. The similarity metric used is the cosine between the query vector and the document vectors. A cosine of 1.0 would indicate that the query vector and the document vector were on top of one another in the space. The cosine metric is similar to a dot product measure except that it ignores the magnitude of the vectors and simply uses the angle between the vectors being compared.

The cosines are sorted, as depicted by processing block 240, and for each of the best N matching documents (typically N=8), the value of the cosine along with organizational information corresponding to the document's group are displayed to the user, as depicted by processing block 250.

Thus, in Deerwester, words, the text objects, and the user queries are processed to extract this underlying meaning and the new, latent semantic structure domain is then used to represent and retrieve information. However, Deerwester fails to suggest any relevance to chemical structures, as neither a recognition of the instant need, nor a recognition of a solution thereto is addressed. Further, for calculation of object similarities LSI uses, for example, singular values to scale the singular vectors for calculation of object similarities.

A need exists, therefore, for a chemical search system method that combines the utility of both a text-based and composition-based search techniques, and additionally/optionally provides synergistic effects therebetween. The present invention fulfills this need by providing such a system and method.

SUMMARY OF THE INVENTION

It is therefore a feature and advantage of the present invention to provide a method and/or system that utilizes a collection of chemical structures, compounds or molecules, and associated textual descriptions thereof, to determine the chemical and textual similarity between the collection of chemical structures and a probe or other proposed chemical structure.

It is a further feature and advantage of the present invention to provide a methodology for calculating the similarity of chemical compounds to chemical and text based probes or other proposed chemical structure.

It is another feature and advantage of the present invention to provide a method and/or system for selecting, based on chemical and text based probes or other proposed chemical structure, chemical compounds that have similar biological or chemical activities or properties, but not necessarily obviously similar structures.

It is another feature and advantage of the present invention to provide a computer readable medium including instructions being executable by a computer, the instructions instructing the computer to generate a searchable representation of chemical structures, given chemical and text based probes or other proposed chemical structure.

The present invention combines both the textual and chemical descriptors of chemical compositions, mixtures, and/or compounds to determine the textual and chemical similarity of those chemical compositions, mixtures, and/or compounds to either an existing descriptor or a user provided descriptor. By providing textual descriptors in addition to the chemical descriptors representing each compound, the present invention advantageously provides an integrated system and method that uncovers relationships between the textual and chemical descriptors that cannot be uncovered using either method. Specifically, as described in detail below, the present invention reveals associations between the text and chemical descriptors that could not be found by combining separate text and chemical analyses, as will be discussed in further detail herein. The following disclosure describes how this merging is done, and provides several retrieval and data mining scenarios using Medline abstracts by way of example.

The method of the present invention, in various embodiments described herein, calculates the similarity between a first chemical or textual descriptor and at least one other chemical and/or textual descriptor in a matrix comprising a plurality of chemical and textual descriptors, and includes the sequential, non-sequential and/or sequence independent steps of creating at least one chemical descriptor and at least one text descriptor for each compound in a collection of compounds, and preparing a descriptor matrix X. In a preferred embodiment, each column of the descriptor matrix represents a document containing textual and chemical descriptions, and each row contains a descriptor associated with at least one document. The numbers stored in the row equal the number of instances of occurrences of each descriptor within each document. It will also be obvious to those skilled in the art that the rows and columns of the descriptor matrix X can be transposed, and that, in such a case, the operations performed on the descriptor matrix X described hereinbelow can be modified accordingly such that results of the operations performed on the transposed matrix are identical to the results of the descriptor matrix X. Then, in a preferred embodiment, a singular value decomposition (SVD) of the descriptor matrix is performed, producing resultant matrices that are used to compute the similarity between a first descriptor and at least one other descriptor. As previously noted, however, other suitable decomposition techniques, such as principal component analysis, can also be utilized. Finally, at least a subset of the at least one other descriptor ranked in order of similarity to the first descriptor is provided as output.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The Detailed Description including the description of a preferred structure as embodying features of the invention will be best understood when read in reference to the accompanying figures wherein.

DETAILED DESCRIPTION OF A PREFERRED EMBODIMENT OF THE INVENTION

Figure 1:
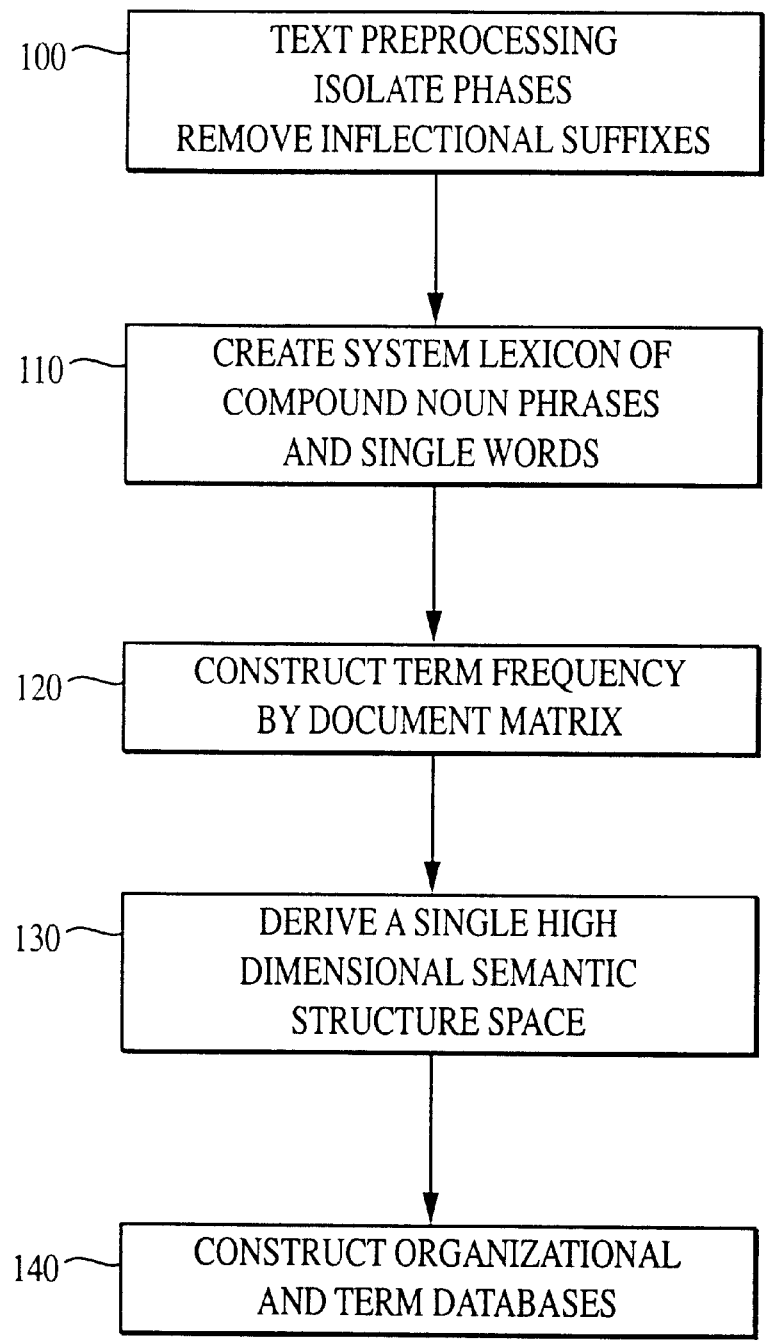
FIG. 1 is a prior art flow chart depicting the processing to generate the "term" and "document" matrices using singular value composition (SVD)
Figure 2:
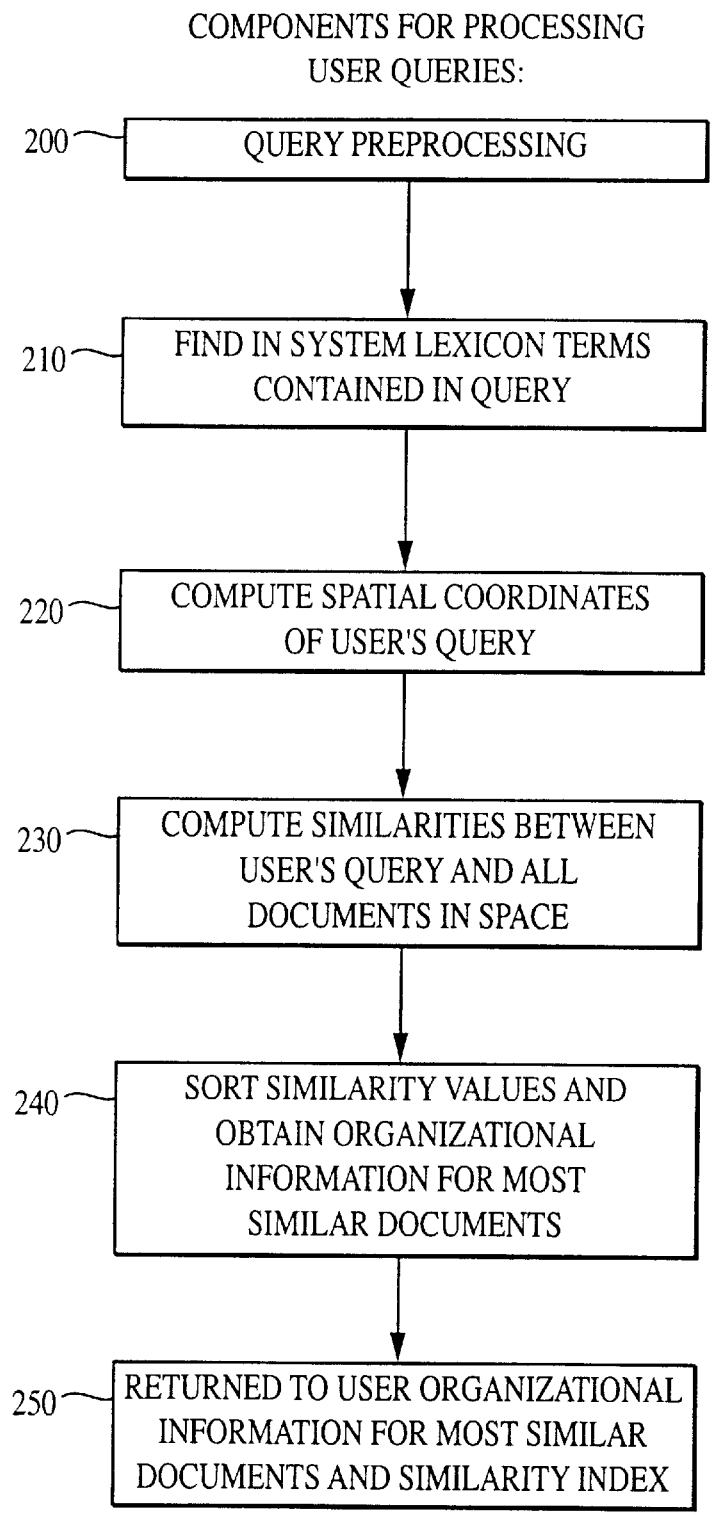
FIG. 2 is a prior art flow chart depicting the processing to of a user's query.

The present invention, in a preferred embodiment, provides a system and method whereby a Singular Value Decomposition (SVD) facilitates the manipulation of key words or descriptors. It should be also understood, however, that other decomposition techniques, such as principal component analysis, can also be utilized.

A matrix textually and compositionally representing every or substantially all chemical structures, compounds, or molecules in a database is generated using standard descriptors, at least some of which are correlated or associated. The SVD technique, or other suitable decomposition technique such as principal component analysis, uncovers these correlations, which are used to rank the chemical structures, compounds, or molecules by textual and/or compositional similarity to the probe or other proposed chemical structure. The SVD technique advantageously identifies descriptors that are related, or substantially related, if not equivalent or substantially equivalent. That is, the descriptors need not be direct or generally accepted synonyms. Rather, they are optionally similar or related terms.

We have discovered that the SVD technique, or other decomposition technique such as principal component analysis, as applied to a chemical context in accordance with the present invention, ranks chemical compounds or structures that may not appear to be obviously structurally similar, but that are, in fact, similar as determined by the associations made in the database of chemical structures or compounds. By way of illustration, many organic compounds are built about carbon rings. In a six-membered ring, for example, using atom pair descriptors, we have determined that not only is there always a carbon atom that is one bond away from another carbon atom, but there is a carbon atom that is two bonds away from another carbon atom as well as a carbon atom that is three bonds away from another carbon atom. In view of this observation, we have recognized that these atom pairs are highly associated, although they are not conceptual synonyms. We have appreciated that the SVD technique facilitates ranking of chemical compounds or structures based on the number and/or degree of these associations.

TIMI Computations

The present invention utilizes a database of molecules and associated textual descriptions thereof. The database is initially represented as a set of vectors, where each vector $V_i = (d_{i1}, d_{i2}, \ldots, d_{in})^T$ consists of the non-negative frequency of occurrence of each respective chemical and/or textual descriptor $d_j$ in document i, where n is preferably the total number of uniquely occurring descriptors in the entire set of documents. A descriptor matrix, X, therefore, is a set of two or more such vectors, i.e., $X = \{V_1, \ldots, V_m\}$, $m \geq 2$, or $$X = \begin{bmatrix} d_{11} & d_{21} & \cdots & d_{m1} \\ d_{12} & d_{22} & \cdots & d_{m2} \\ \vdots & \vdots & \vdots & \vdots \\ d_{1n} & d_{2n} & \cdots & d_{mn} \end{bmatrix} \text{ word or chemical descriptors}$$

text and/or chemical abstract where X comprises m columns and n rows. It will also be obvious to those skilled in the art that the rows and columns of the descriptor matrix X can be transposed, and that, in such a case, the operations performed on the descriptor matrix X described hereinbelow can be modified accordingly such that results of the operations performed on the transposed matrix are identical to the results of the descriptor matrix X.

The present invention in its preferred embodiment advantageously utilizes the SVD of X to produce a reduced dimensional representation of the original matrix. Let the SVD of X in $R^{m \times n}$ be defined as $X = P \Sigma Q^T$ where P is a mxr matrix, called the left singular matrix (r is the rank of X), and its columns are the eigenvectors of $XX^T$ corresponding to nonzero eigenvalues. Q is a nxr matrix, called the right singular matrix, whose columns are the eigenvectors of $X^T X$ corresponding to nonzero eigenvalues. $\Sigma$ is a rxr diagonal matrix=diag($\sigma_1, \sigma_2, \ldots \sigma_r$) whose nonzero elements, called singular values, are the square roots of the eigenvalues and have the property that $\sigma_1 \geq \sigma_2 \geq \ldots \geq \sigma_r$. Thus, $$\begin{bmatrix} d_{11} & d_{21} & \cdots & d_{n1} \\ d_{12} & d_{22} & \cdots & d_{n2} \\ \vdots & \vdots & \vdots & \vdots \\ d_{1n} & d_{2n} & \cdots & d_{mn} \end{bmatrix} \xrightarrow{SVD}$$

$$\begin{bmatrix} P_{11} & \cdots & P_{r1} \\ P_{12} & \cdots & P_{r2} \\ \vdots & \vdots & \vdots \\ P_{1n} & \cdots & P_{rn} \end{bmatrix} \cdot \begin{bmatrix} \sigma_1 & & \\ & \ddots & \\ & & \sigma_r \end{bmatrix} \cdot \begin{bmatrix} Q_{11} & Q_{12} & \cdots & Q_{1m} \\ \vdots & \vdots & \vdots & \vdots \\ Q_{r1} & Q_{r2} & \cdots & Q_{rm} \end{bmatrix}$$

The $k^{th}$ rank approximation of X, $X_k$, for k<r, $\sigma_{k+1} \ldots \sigma_r$ set to 0, can be efficiently computed using variants of the standard Lanczos algorithm (see "SVDPACKC (Version 1.0) User's Guide", University of Tennessee, Knoxville, Department of Computer Science Technical Report CS-93-194, revised March 1996, Berry, et al.), incorporated herein by reference. $X_k$ is the matrix of rank k which is the closest to X in the least squares sense, is called a partial SVD of X, and is defined as $X_k = P_k \Sigma_k Q^T_k$.

The TIMI similarity of two chemical descriptors, $d_i$ and $d_j$, is calculated by computing the dot product between the $i^{th}$ and $j^{th}$ rows of the matrix $P_k$, and is provided by the formula $$\sum_{x=1}^{k} \frac{P_{ix}}{|P_i|} \cdot \frac{P_{jx}}{|P_j|}.$$

The TIMI similarity between two documents (e.g., abstracts, or other text description) represented by vectors $V_i$ and $V_j$, is calculated by computing the dot product between the $i^{th}$ and $j^{th}$ rows of the matrix $Q_k$, and is provided by the formula $$\sum_{x=1}^{k} \frac{Q_{ix}}{|Q_i|} \cdot \frac{Q_{jx}}{|Q_j|}.$$

The TIMI similarity of a descriptor, $d_i$ to a document or other text description, $V_j$ is calculated by computing the dot product between the $i^{th}$ row of the matrix $P_k$ and the $j^{th}$ row of the matrix $Q_k$ and is provided y the formula $$\sum_{x=1}^{k} \frac{P_{ix}}{|P_i|} \cdot \frac{Q_{jx}}{|Q_j|}.$$

Finally, the TIMI similarity of an ad hoc query to the descriptors and molecules in the database is calculated by first projecting the query into the k-dimensional space of the partial SVD and then treating the projection as a molecule for between and within comparisons. The projection of a query vector, q, is defined as $V_q = q^T P \Sigma^{-1}_k$.

It should be noted that, unlike the method disclosed in Deerwester, TIMI does not use the singular values to scale the singular vectors. Instead, TIMI uses the identity matrix, I, when calculating similarities, whereas Deerwester utilizes $\Sigma_k$. Ignoring the scaling component $\Sigma_k$ improves the ability to select similar molecules regardless of whether the probe's descriptors are well represented in the database.

Methodology

There are two phases of operation associated with TIMI. The first phase involves constructing a TIMI database from a collection of documents or textual descriptions, and the second phase involves querying that database.

Constructing a TIMI database

Figure 3:
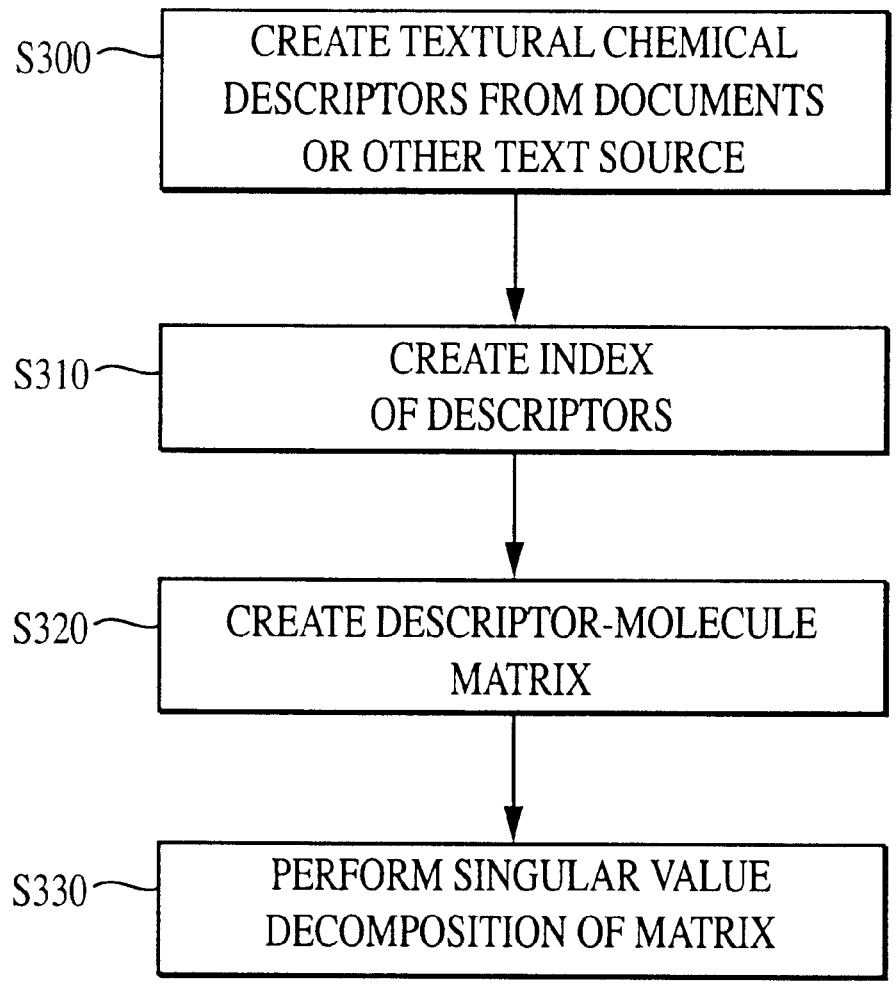
FIG. 3 is a flow chart depicting the processes of creating a TIMI database.

Generating a TIMI database includes the following sequential, non-sequential, or sequence independent steps. Referring to FIG. 3, in step S300, a user and/or a computer generates or creates chemical and textual descriptors for each compound represented in the database.

The textual descriptors may, for example, originate from a collection of documents, or other text source, in, say, ASCII format or other suitable format. A textual representation of the chemical descriptors is also added to the textual descriptors. These documents might be, for example, journal articles, MEDLINE abstracts, internal progress reports, memos, trip reports, meeting minutes, and the like. The native formats of these documents might require the use of conversion software to generate ASCII versions. Preferably, the ASCII corpus is then "normalized" by, for example, removing unnecessary punctuation, stemming words, standardizing case, and removing formatting.

There are some idiosyncrasies of medical texts that make this step more challenging than it might be if texts were being analyzed from other disciplines. For example, we have discovered the systematic chemical names described in *Chemical Abstracts* (Chemical Abstracts Service, 1997) or *International Union of Pure and Applied Chemistry* (IUPAC) (Panico et al., 1994) may contain parentheses, brackets, commas, single quotes, colons, hyphens, pluses, periods, and the like. Gene and protein names are often short acronyms which can be confused with other words when case has been normalized. Database identifiers and accession numbers can also obfuscate normalization. In practice, Perl scripts with access to specially crafted lexicons of chemical, gene, protein names and identifiers can, for example, be utilized to perform the text processing necessary to normalize the input documents. It is preferred, but not essential to practicing the invention, that the terms of each normalized document be compared against an index of chemical compound names with known chemical structure.

In step S310, the user and/or the computer generates or creates an index relating the columns of the matrix X, each of which correspond to a particular document, to the textual and chemical descriptors, and another index relating the rows of the matrix to the textual and chemical descriptors.

In step S320, the user and/or the computer generates or creates a textual and chemical descriptor matrix X representing the compounds in the documents. In step S330, the user and/or the computer performs SVD on the descriptor matrix X.

For example, consider the following abstract title as a document: "Butein, a specific protein tyrosine kinase inhibitor".

After normalization, this document would contain the seven words "butein", "a", "specific", "protein", "tyrosine", "kinase", and "inhibitor". The structure for butein, is shown below.

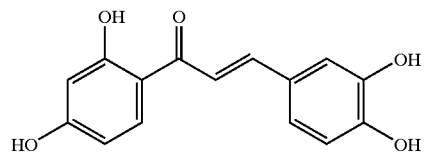

The butein connection table generates fifty-six atom pair (AP) and topological torsion (TT) descriptors, a portion of which are shown in Table 1. The descriptors can be thought of as terms, and merged directly into the text.

TABLE 1

Ten of the Fifty-six Chemical Descriptors of Butein and Their Term Frequencies

| Descriptor | Number of Occurrences |
| --- | --- |
| c21c2101 | 3 |
| c21c2102 | 4 |
| c21c2103 | 6 |
| c21c2104 | 4 |
| c21c2105 | 2 |
| c21c2106 | 2 |
| c21c2107 | 5 |
| c21c2108 | 2 |
| c21c31c21c21 | 5 |
| c21c31c21c21 | 3 |

At this stage of the processing, the representation of the title of the abstract would be the seven English words (each occurring once), in addition to the fifty-six chemical terms (each with their own frequencies), for a total of sixty-three terms. Note that the word "a" still exists because stop word removal has yet to be performed.

In accordance with step S320, the merged text and chemistry is then recast to create a matrix where each row preferably represents a unique term, each column represents a document or text source, and the value of element <i,j> is the number of occurrences of term$_i$ in document$_j$, or text source. Term$_i$, therefore, may occur any number of times in document$_j$, or text source. Stop words can be generated, for example, from inverse document frequency (idf) scores (for example, any term occurring in more than 50% of the documents is removed from consideration as a row of the matrix). A singular value decomposition of this matrix is performed resulting in the three SVD matrices (P, $\Sigma$, and $Q^T$) used in calculating similarities, as will be described in further detail herein.

Searching the TIMI Database

Figure 4:
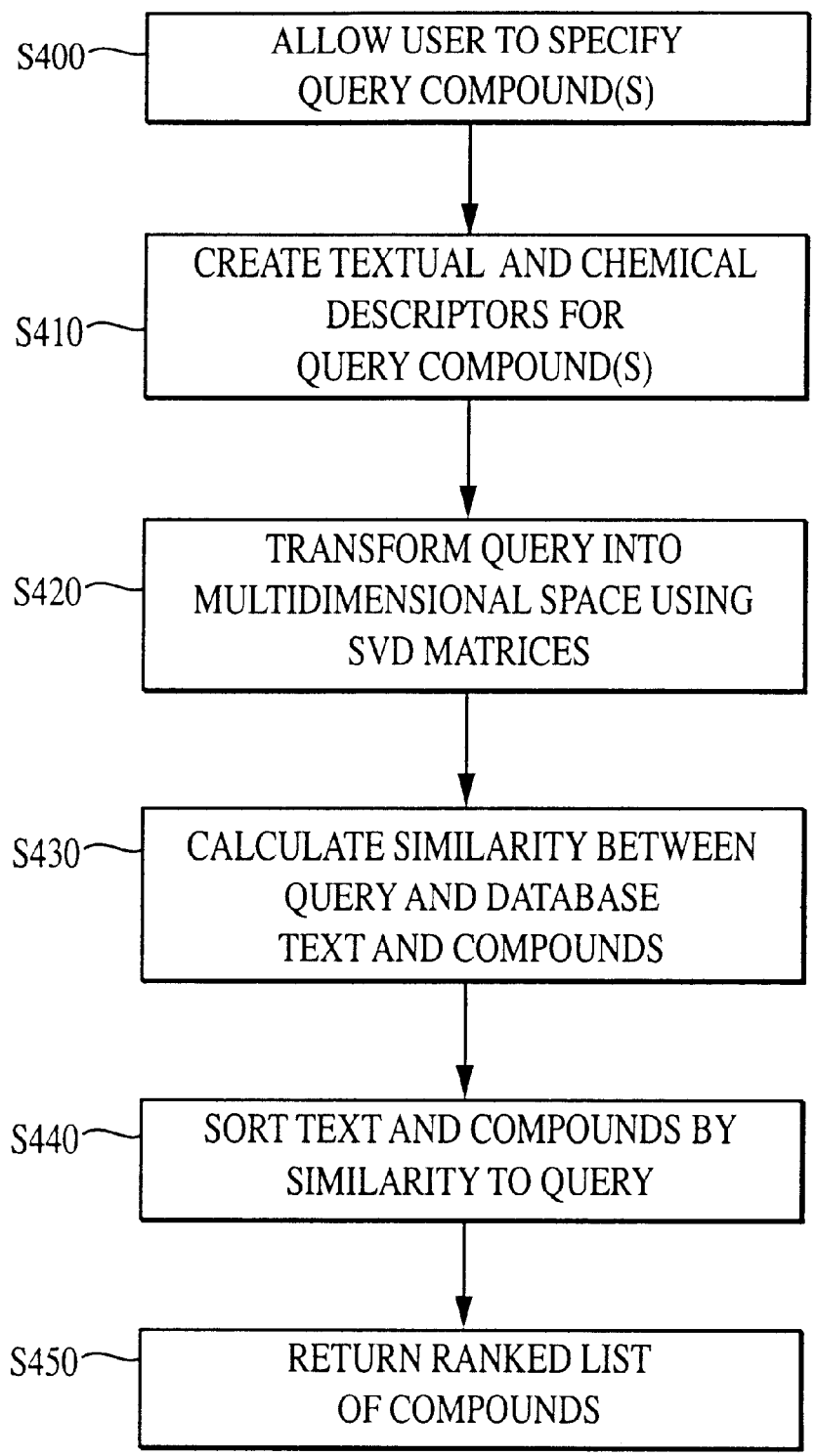
FIG. 4 is a flow chart depicting the processes according to a first preferred embodiment of the present invention.

As shown in FIG. 4, searching a TIMI database is carried out as follows. In step S400, the user specifies one or more words and/or chemical structures as a probe. The connection table of a probe molecule, text, or multiple molecules or text in the case of a joint probe, is converted to the descriptor set of the TIMI database to create a feature, or column, vector for the probe in step S410. In step S420, a pseudo-object is then obtained as described above for some k, as specified by the user. The normalized dot products of each descriptor (row of $P_k$) and each document (column of $Q_k$) with the pseudo-object are optionally calculated in step S430, and the resulting values are optionally sorted, preferably in descending order in step S440, thus maintaining the index of the descriptor and document responsible for that value. The user is then presented, for example, with a list of the top ranked documents, cutoff at a user defined threshold (e.g., the top 300 or 1000 compounds) in step S450.

By varying the number of singular values, based at least in part on the choice of k, the user, as will be recognized by those skilled in the art, controls the level of fuzziness of the search in terms of fuzzy logic. Larger values of k are less fuzzy than smaller values thereof.

Figure 5:
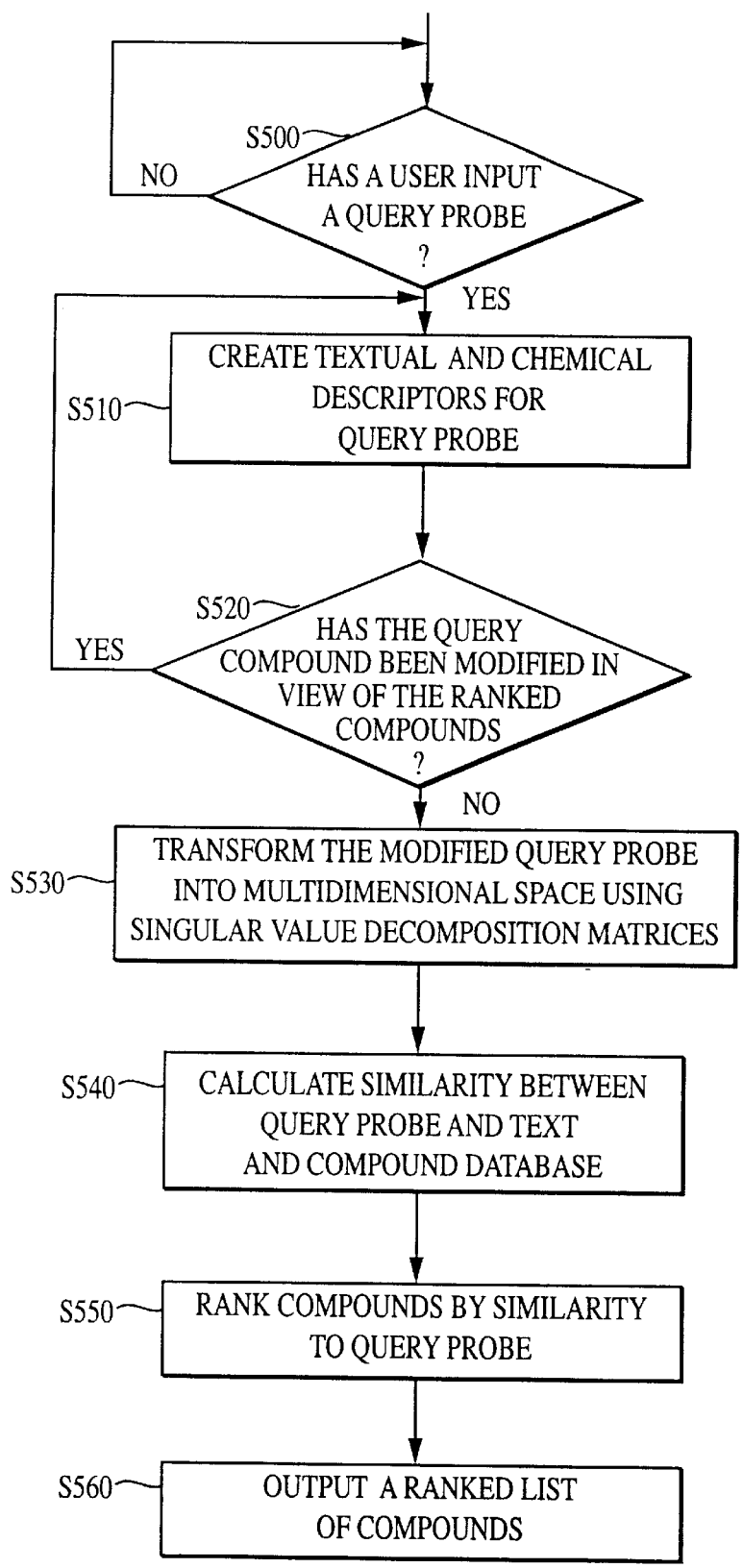
FIG. 5 is a flow chart of a second preferred embodiment of the present invention.

FIG. 5 shows a flow chart of an alternative embodiment of a method consistent with the instant invention. The method includes the following sequential, non-sequential, or sequence independent steps. In step S500, a computer determines whether a user has input a query compound probe or query joint probe. If yes, in step S510, the computer generates chemical and textual descriptors for the query document(s) or text and compound probe or joint probe. In step S520, the computer determines whether the user has modified the query in view of the generated results. The user can select ranked compounds and add them to the original probe and re-execute the search. If yes, flow returns to step S510. Otherwise, in step S530, the computer transforms the modified query probe into multi-dimensional space using singular value decomposition matrices. In step S540, the computer calculates the similarity between the query probe and the chemical structures and textual descriptions thereof in the compounds database. In step S550, the computer ranks the compounds in the compound database by similarity to the query probe. In step S560, the computer outputs a ranked list of compounds in a standard manner, for example, via a standard computer monitor or via a standard printer.

Mining the TIMI Database

Whereas database searching is accomplished by simply providing the ranked list of documents, mining the database is a bit more interesting. One reason TIMI was developed is to assist medicinal chemists in their efforts to discover new lead compounds and to understand more about chemical structures and their relationships to the biological structures mentioned in the literature. Therefore, we have investigated specialized mining tasks that can be addressed with TIMI, including the extraction of chemical similarities and biological properties and associations.

For example, one can project a chemical structure into the k-dimensional space and then examine the list of compound identifiers that are closely similar. Or, one can project two or more chemical structures into the k-dimensional space and calculate their cosine similarities directly. Both of these operations involve comparison between chemical structures, although the similarity has been altered and perhaps enhanced by the presence of the surrounding text.

TIMI can also calculate the similarity of a chemical probe to classes of terms in an effort to infer certain properties or relationships. After presenting a chemical structure probe, the sorted list of terms can be examined to see what are the highest ranked therapeutic terms, disease names, toxicity liabilities, adverse effects, and the like. Suppose it is determined that the rankings of therapeutic terms (terms related to therapeutic categories) heavily favor one category over all others. If it is found that in the list of most similar terms to a particular compound are the words "cholesterol", "lipid", and "triglyceride", it might be inferred that there is some component of the structure of the compound which is similar to the structures of compounds mentioned in documents (e.g., abstracts) about hypercholestoremia. The same is true for highly ranked disease names or toxicity related terms such as "mutagen(ic)", "carcinogen(ic)", "hepatotoxic(ity)", etc.

Alternatively, TIMI can determine which chemical compounds or descriptors are most similar to certain terms. For example, consider the following question: Which chemical descriptors are most associated with the terms "carcinogen" and "carcinogenic"? In order to answer this question, a probe vector is created with two non-zero frequencies for each term. The list of ranked compounds is then examined, specifically for the highest ranked chemical descriptors. The associated scores of the descriptors can then be used to color the atoms of compounds of interest. Coloring the atoms visually indicates which components of the compound are associated with the property. This approach can be taken to any property that is described in the corpus.

Early identification of potential uses for and/or problems with new drugs can save pharmaceutical companies millions of dollars in research and development costs. TIMI allows the researcher to take advantage of past experiments described in the literature to gain some advantage over these concerns. We examine some of these relationships in the context of a corpus of Medline abstracts in the next section.

MEDLINE Experiments

A set of 11,571 MEDLINE abstracts using the term "drug" and published within a three month period of 1998 were extracted from the MEDLINE database. The text was preprocessed in order to identify chemical name identifiers and to merge the chemical descriptors of recognized compounds into the appropriate abstract(s). 2,876 unique compound identifiers whose connection tables exist within a Merck & Co., Inc. proprietary database were found within 6,929 abstracts. 4,642 abstracts did not have any identifiable structure associated with them. The ten most frequently cited compounds were glutathione (181), dopamine (179), glucose (157), cholesterol (141), cisplatin (132), serotonin (131), cocaine (127), doxorubicin (111), adenosine (110), and morphine (109). The atom pair and topological torsion descriptors of these compounds were added to the text. The list of chemical and textual descriptors was then used to create a term/abstract matrix. The dimensions of this matrix were 42,566 unique terms x 11,571 abstracts. The Lanzcos iterative SVD algorithm (see Berry, et al. 1996) was used to produce 217 singular vectors. Hereinafter this database will be referred to as the $TIMI_{TC}$ database (TC stands for "text and chemistry").

Two other databases were constructed in addition to the $TIMI_{TC}$ database. A database of just the original terms (i.e., no chemical representation), was created ($TIMI_T$), as was a database of just the chemical structures ($TIMI_C$). These two additional databases were generated for the comparison studies described hereinbelow.

Three different sets of queries were then posed to the databases. The first set involved chemical structure queries, the second set involved terms, and the third set involved both a structure and one or more terms. Obviously, structure queries can not be posed to the text only database and term queries can not be posed to the structure only database. The purpose of these three sets was to investigate the differences in retrieval and mining afforded by each database.

Chemical Structure Queries

One structure query involves avasimibe (CI-1011), a cholesterol lowering drug, the structure of which is shown below.

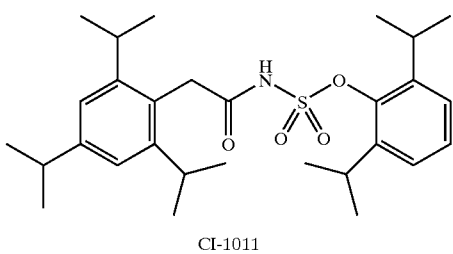

CI-1011

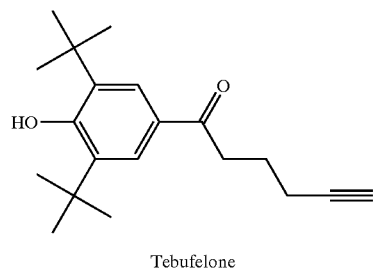

Tebufelone

Avasimibe is mentioned by its company code, ci-1011, a total of twelve times in two different abstracts, MED306 and MED2600. A search of TIMI$_{TC}$ with the structure of ci-1011 and setting k=100 resulted in the lists of ranked documents and terms shown in Table 2.

TABLE 2

Top Ten Scoring Documents and Terms
for the ci-1011 Structural Probe Against TIMI$_{TC}$

| Document | Score | Term | Score |
|---|---|---|---|
| MED306 | 0.885 | ci-1011 | 0.881 |
| MED2600 | 0.840 | s42o20c31c31 | 0.876 |
| MED7277 | 0.672 | b-100 | 0.869 |
| MED6244 | 0.670 | lp(a) | 0.838 |
| MED2036 | 0.637 | streak | 0.829 |
| MED4582 | 0.634 | lipoprotein(a) | 0.816 |
| MED20 | 0.629 | aa.wl.com | 0.809 |
| MED8477 | 0.622 | lowell | 0.768 |
| MED8359 | 0.620 | ldl-c | 0.735 |
| MED8566 | 0.619 | fascicularis | 0.664 |

As expected, MED306 and MED2600 are the top ranked documents. MED7277, whose title is "Wavelet Analysis of Acoustically Evoked Potentials During Repeated Propofol Sedation," does not mention ci-1011 but does discuss propofol, a compound which is arguably a sub-structure of ci-1011.

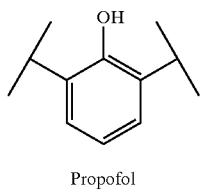

Propofol

Propofol, the chemical structure of which is as shown above, is an anesthesia agent developed in the early 1990's and has no direct connection to ci-1011. However, because of the similar structure it is possible that propofol and ci-1011 might share some biologic activities. The next two abstracts, MED6244 and MED2036, also discuss propofol.

The sixth ranked abstract, MED4582, discusses tebufelone, the chemical structure of which is as shown above.

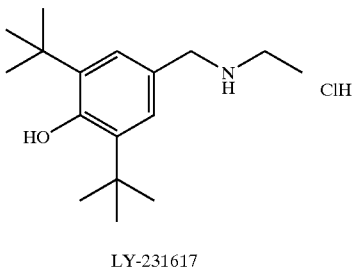

LY-231617

Abstracts seven, eight, and ten also mention propofol. Abstract nine, MED8359, discusses compound LY-231617, the chemical structure of which is as shown above. LY-231617 was initially developed to treat stroke and as a neuro-protective agent.

The top ten terms can also tell us something about this compound. The term ci-1011 is the highest ranked term which, at first glance, might not appear to be particularly interesting. However, recall that our probe was only the chemical descriptors of the chemical structure of ci-1011, and did not include the word "ci-1011". The second term shown in Table 2, s42o20c31c31, is a topological torsion chemical descriptor. B-100, the third term shown in Table 2, is an apolipoprotein, as are lp(a) and lipoprotein(a), which are certainly related to the use of the compound. ci-1011 is effective in the prevention and regression of the aortic fatty streak area in hamsters. The URL aa.wl.com was the home page of Warner Lambert's Ann Arbor, Mich. research site. Lowell is a city in Massachusetts where one of the author's of abstract MED2600 is affiliated. Ldl-c (low-density lipoprotein cholesterol) and fascicularis in Macaca fascicularis (Java Macaque), a monkey used in cholesterol-lowering experiments, are both described in MED306.

The same query can be performed against the chemistry database TIMI$_C$. In this case the similarity of ci-1011 to each of the other compounds found in the abstracts is computed. Those articles which mention the high-ranking compounds are then retrieved. Table 3 shows the top ten ranking compounds and their cosine similarity scores.

TABLE 3

Top Ten Most Similar Compounds to the ci-1011 Structural
Probe Against TIMI$_C$

| Compound | Score |
|---|---|
| ci-1011 | 1.000 |
| propofol | 0.630 |

TABLE 3-continued

Top Ten Most Similar Compounds to the ci-1011 Structural
Probe Against $TIMI_C$

| Compound | Score |
|---|---|
| tebufelone | 0.556 |
| LY-231617 | 0.533 |
| myxothiazol | 0.499 |
| probucol | 0.492 |
| anastrozole | 0.447 |
| arimidex | 0.447 |
| pyridoxal | 0.431 |
| terbinafine | 0.422 |

As seen, many of the same compounds arising from abstracts selected from $TIMI_{TC}$ appear as the most similar compounds in the chemistry only search. Of course, there is no way to retrieve abstracts which do not have a chemical structure associated to them. Moreover, there is no association between the terms and the chemical descriptors that can be examined.

Text Queries

Text queries can be applied to both $TIMI_{TC}$ and $TIMI_T$. It is instructive to continue the investigation of ci-1011 because it can then be seen how the text only query using the name of the compound compares to its structural query. Table 4 lists the abstracts and terms most similar to the term "ci-1011" found in $TIMI_T$.

TABLE 4

Top Ten Scoring Documents and Terms
for the Term "ci-1011" Probe Against $TIMI_T$

| Document | Score | Term | Score |
|---|---|---|---|
| MED2600 | 0.787 | ci-1011 | 0.986 |
| MED306 | 0.783 | streak | 0.842 |
| MED8218 | 0.557 | ldl-c | 0.825 |
| MED6229 | 0.487 | b-100 | 0.743 |
| MED6232 | 0.476 | anit-atherogenic | 0.616 |
| MED1171 | 0.443 | cholesterol | 0.607 |
| MED11196 | 0.438 | sequestering | 0.605 |
| MED11474 | 0.430 | hypercholesterolemic | 0.571 |
| MED4461 | 0.416 | caveolin | 0.569 |
| MED2030 | 0.415 | low-density | 0.554 |

In this case we see that while the first two ranked documents are the same as the ci-1011 structural query against $TIMI_{TC}$ (shown in Table 2), the rest of the documents are different due to the influence of the chemical descriptors. The first four terms are also found in the top ten terms of the $TIMI_{TC}$ run, but after that they are different. Clearly, the chemical descriptors are creating a qualitative difference in the rankings.

If the term "ci-1011" is used to probe $TIMI_{TC}$ instead of the structure of ci-1011, the results shown in Table 5 are obtained.

TABLE 5

Top Ten Scoring Documents and Terms for the
Term "ci-1011" Probe Against the $TIMI_{TC}$ Database

| Document | Score | Term | Score |
|---|---|---|---|
| MED306 | 0.884 | ci-1011 | 0.985 |
| MED2600 | 0.876 | s42o20c31c31 | 0.985 |
| MED2987 | 0.587 | streak | 0.961 |
| MED9743 | 0.573 | b-100 | 0.936 |
| MED8566 | 0.565 | aa.wl.com | 0.934 |
| MED7277 | 0.556 | lp(a) | 0.926 |
| MED6244 | 0.574 | ldl-c | 0.901 |
| MED20 | 0.546 | lipoprotein(a) | 0.901 |
| MED8359 | 0.534 | lowell | 0.897 |
| MED9468 | 0.531 | anti-atherogenic | 0.885 |

Here it is seen that these results are more like those in Table 2, suggesting that the term "ci-1011" and the structure of ci-1011 are virtually synonyms in $TIMI_{TC}$.

Text and Chemical Structure Queries

Finally, we can perform one special search in $TIMI_{TC}$ that can not be performed in either $TIMI_T$ or $TIMI_C$ individually—a combined structure and text query. Combining both query types is advantageous because one can "tweak" a structural search with carefully chosen keywords. For example, suppose the user is most interested in the possibility of toxicity with a given compound. She can then add terms related to toxicity to the structural query, thereby ranking documents which discuss toxicity issues more highly.

Discussion

Several interesting points arose from these experiments. The terms related to the structural query of ci-1011 in the $TIMI_{TC}$ database are quite remarkable (see Table 2). The system uncovered associations between the chemical descriptors of the probe and many English words which are obviously related to this cholesterol-lowering drug. The associations are along many different conceptual dimensions: the name of the probe, ci-1011; the chief mechanism of transportation of cholesterol into arterial walls, lipoproteins; the species name of an animal used in testing the compound, fascicularis; and affiliation information, Lowell, and aa.wl.com. Many other obviously related words are also found just outside the top ten, such as, anti-atherogenic (12), apolipoprotein(a) (14), and hypercholesterolemic (15). There are other words whose rankings are not so obvious and we believe that some of these terms might provide new insights.

The compounds found in highly ranked abstracts of the same search, propofol, tebufelone, and LY-231617, are also interesting because all three are from different therapeutic categories. Therefore, it is less likely that a medicinal chemist interested in cholesterol-lowering drugs would know of their existence. This might be especially poignant given the fact that development of tebufelone was dropped due to liver toxicity.

Conclusion

The experiments above illustrate the advantages of merging textual and chemical descriptors over either text or chemistry individually. A text only database can not benefit from associations which are made across chemical structure. Specifically, it can not relate those textual terms to chemical features. Further, in a text only database; one can only retrieve documents concerning the compounds explicitly mentioned in the text. Similarly, a chemistry only database can not benefit from associations which are made across the text nor can it index abstracts which do not have any chemical structures mentioned in them. The TIMI method and system leverages the contextual knowledge developed by scientists within the pharmaceutical, biological, and medicinal chemistry community.

Representative General Purpose Computer

Figure 6:
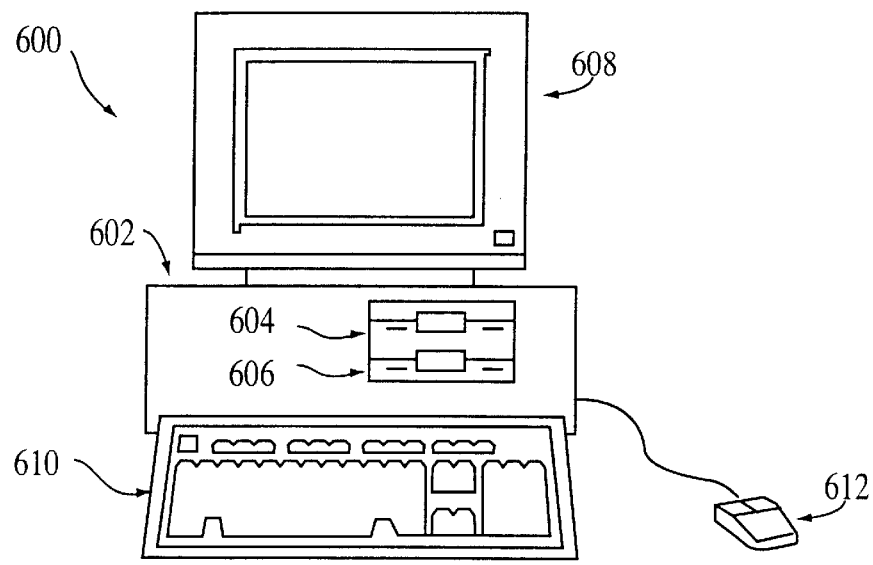
FIG. 6 is an illustrative embodiment of a computer and assorted peripherals.

FIG. 6 is an illustration of a main central processing unit for implementing the computer processing in accordance with a computer implemented embodiment of the present invention. The procedures described herein are presented in terms of program procedures executed on, for example, a computer or network of computers.

Viewed externally in FIG. 6, a computer system designated by reference numeral 400 has a computer 602 having disk drives 604 and 606. Disk drive indications 604 and 606 are merely symbolic of a number of disk drives which might be accommodated by the computer system. Typically, these would include a floppy disk drive 604, a hard disk drive (not shown externally) and a CD ROM indicated by slot 606. The number and type of drives varies, typically with different computer configurations. Disk drives 604 and 606 are in fact optional, and for space considerations, are easily omitted from the computer system used in conjunction with the production process/apparatus described herein.

The computer system also has an optional display 608 upon which information is displayed. In some situations, a keyboard 610 and a mouse 602 are provided as input devices to interface with the central processing unit 602. Then again, for enhanced portability, the keyboard 610 is either a limited function keyboard or omitted in its entirety. In addition, mouse 612 optionally is a touch pad control device, or a track ball device, or even omitted in its entirety as well. In addition, the computer system also optionally includes at least one infrared transmitter and/or infrared received for either transmitting and/or receiving infrared signals, as described below.

Figure 7:
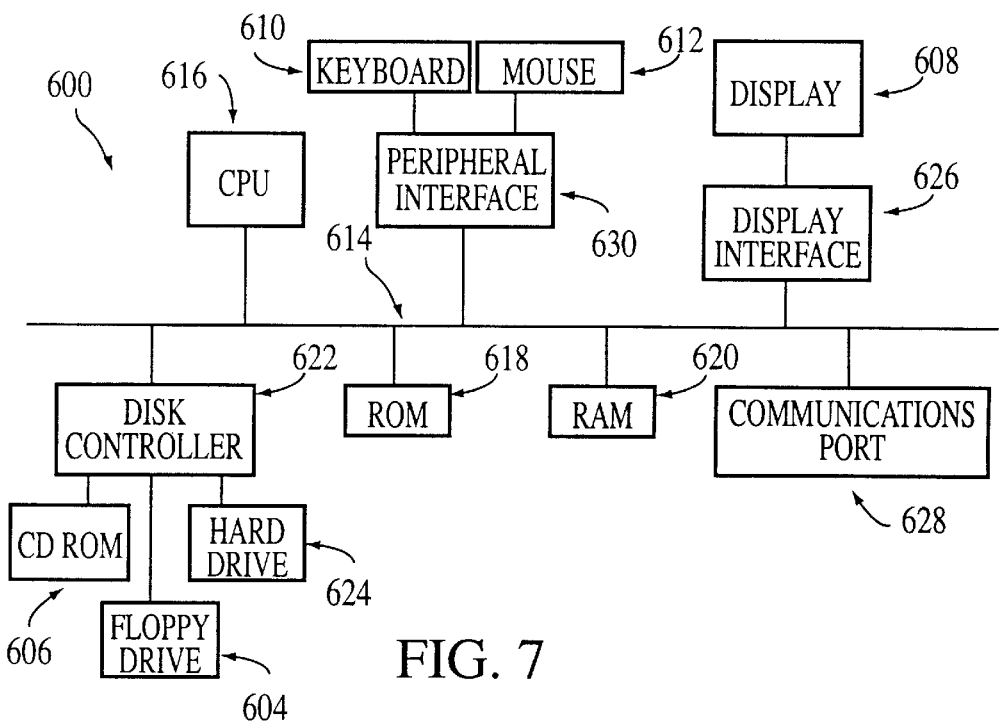
FIG. 7 is an illustrative embodiment of internal computer architecture consistent with the instant invention.

FIG. 7 illustrates a block diagram of the internal hardware of the computer system 600 of FIG. 6. A bus 614 serves as the main information highway interconnecting the other components of the computer system 600. CPU 616 is the central processing unit of the system, performing calculations and logic operations required to execute a program. Read only memory (ROM) 618 and random access memory (RAM) 620 constitute the main memory of the computer. Disk controller 622 interfaces one or more disk drives to the system bus 614. These disk drives are, for example, floppy disk drives such as 604, or CD ROM or DVD (digital video disks) drive such as 606, or internal or external hard drives 624. As indicated previously, these various disk drives and disk controllers are optional devices.

A display interface 626 interfaces display 608 and permits information from the bus 614 to be displayed on the display 608. Again as indicated, display 608 is also an optional accessory. For example, display 608 could be substituted or omitted. Communications with external devices, for example, the components of the apparatus described herein, occurs utilizing communication port 628. For example, optical fibers and/or electrical cables and/or conductors and/or optical communication (e.g., infrared, and the like) and/or wireless communication (e.g., radio frequency (RF), and the like) can be used as the transport medium between the external devices and communication port 628. Peripheral interface 630 interfaces the keyboard 610 and the mouse 612, permitting input data to be transmitted to the bus 614. In addition to the standard components of the computer, the computer also optionally includes an infrared transmitter and/or infrared receiver. Infrared transmitters are optionally utilized when the computer system is used in conjunction with one or more of the processing components/stations that transmits/receives data via infrared signal transmission.

Instead of utilizing an infrared transmitter or infrared receiver, the computer system optionally uses a low power radio transmitter and/or a low power radio receiver. The low power radio transmitter transmits the signal for reception by components of the production process, and receives signals from the components via the low power radio receiver. The low power radio transmitter and/or receiver are standard devices in industry.

Figure 8:
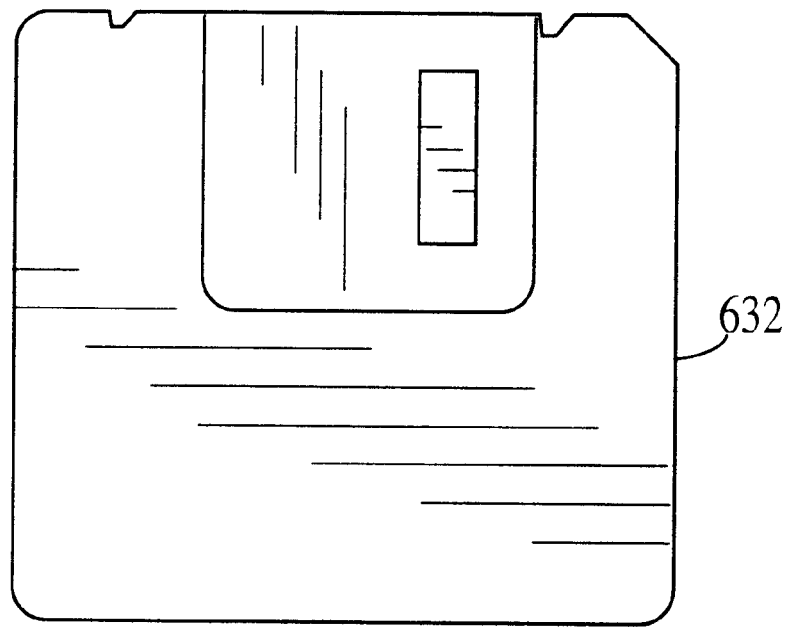
FIG. 8 is an illustrative embodiment of a memory medium.

FIG. 8 is an illustration of an exemplary memory medium 632 which can be used with disk drives illustrated in FIGS. 5 and 7 Typically, memory media such as floppy disks, or a CD ROM, or a digital video disk will contain, for example, a multi-byte locale for a single byte language and the program information for controlling the computer to enable the computer to perform the functions described herein. Alternatively, ROM 618 and/or RAM 620 illustrated in FIGS. 5 and 7 can also be used to store the program information that is used to instruct the central processing unit 416 to perform the operations associated with the production process.

Although computer system 600 is illustrated having a single processor, a single hard disk drive and a single local memory, the system 600 is optionally suitably equipped with any multitude or combination of processors or storage devices. Computer system 600 is, in point of fact, able to be replaced by, or combined with, any suitable processing system operative in accordance with the principles of the present invention, including sophisticated calculators, and hand-held, laptop/notebook, mini, mainframe and super computers, as well as processing system network combinations of the same.

Conventional processing system architecture is more fully discussed in *Computer Organization and Architecture,* by William Stallings, MacMillan Publishing Co. (3rd ed. 1993); conventional processing system network design is more fully discussed in *Data Network Design,* by Darren L. Spohn, McGraw-Hill, Inc. (1993), and conventional data communications is more fully discussed in *Data Communications Principles,* by R. D. Gitlin, J. F. Hayes and S. B. Weinstain, Plenum Press (1992) and in *The Irwin Handbook of Telecommunications,* by James Harry Green, Irwin Professional Publishing (2nd ed. 1992). Each of the foregoing publications is incorporated herein by reference. Alternatively, the hardware configuration is, for example, arranged according to the multiple instruction multiple data (MIMD) multiprocessor format for additional computing efficiency. The details of this form of computer architecture are disclosed in greater detail in, for example, U.S. Pat. No. 5,163,131; Boxer, A., "Where Buses Cannot Go", IEEE Spectrum, February 1995, pp. 41–45; and Barroso, L. A. et al., "RPM: A Rapid Prototyping Engine for Multiprocessor Systems", IEEE Computer February 1995, pp. 26–34, each of which are incorporated herein by reference.

In alternate preferred embodiments, the above-identified processor, and, in particular, CPU 616, may be replaced by or combined with any other suitable processing circuits, including programmable logic devices, such as PALs (programmable array logic) and PLAs (programmable logic arrays). DSPs (digital signal processors), FPGAs (field programmable gate arrays), ASICs (application specific integrated circuits), VLSIs (very large scale integrated circuits) or the like.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention. While the foregoing invention has been described in detail by way of illustration and example of preferred embodiments, numerous modifications, substitutions, and alterations are possible without departing from the scope of the invention defined in the following claims

Having thus described our invention, what we claim as new and desire to secure by Letters Patent is as follows:

1. A method of calculating similarity or substantial similarity between a first chemical descriptor and at least one other chemical descriptor in a matrix representing a plurality of chemical and textual descriptors, comprising the steps of:
   (a) creating at least one chemical descriptor and at least one textual descriptor for a plurality of compounds in a collection of compounds;
   (b) preparing a descriptor matrix X, wherein the descriptor matrix comprises:
      at least one text source containing textual and chemical descriptions, and;
      at least one descriptor associated with each respective text source,
      wherein the entries in the descriptor matrix indicate a relevancy of a descriptor to a respective text source;
   (c) performing a singular value decomposition (SVD) of the descriptor matrix to produce resultant matrices;
   (d) using at least one of the resultant matrices to compute the similarity between the first chemical descriptor $d_i$ and the at least one other chemical descriptor $d_j$; and
   e) outputting at least a subset of the at least one other chemical descriptor ranked in order of similarity to the first chemical descriptor.

2. The method as recited in claim 1, wherein said creating step includes generating atom pair and topological torsion descriptors from chemical connection tables of the collection of compounds.

3. The method as recited in claim 1, wherein said creating step includes creating an index of descriptors and an index of compounds in the collection.

4. The method as recited in claim 1 wherein said performing step comprises the step of:
   generating matrices P, $\Sigma$, and $Q^T$, such that descriptor matrix $X=P\Sigma Q^T$, wherein
      P is a mxr matrix, called the left singular matrix (r is the rank of X), and its columns are the eigenvectors of $XX^T$ corresponding to nonzero eigenvalues;
      Q is a nxr matrix, called the right singular matrix, whose columns are the eigenvectors of $X^TX$ corresponding to nonzero eigenvalues; and
      $\Sigma$ is a rxr diagonal matrix whose nonzero elements, $\sigma_1$, $\sigma_2$, ..., $\sigma_r$ called singular values, are the square roots of the eigenvalues and have the property that $\sigma_1 \geq \sigma_2 \geq ... \geq \sigma_r$.

5. The method as recited in claim 4 wherein said computing step comprises the step of computing the dot product between the $i^{th}$ and $j^{th}$ rows of the matrix $P\Sigma$.

6. The method as recited in claim 1 wherein the first chemical descriptor is initially an ad hoc query vector q, further comprising the step of:
   determining a matrix $X_k$, wherein $X_k$ is the matrix of rank k which is equivalent to $P_k\Sigma_k Q^T_k$, and is the least squares closest to X; and
   projecting the ad hoc query vector onto $X_k$.

7. The method as recited in claim 6 wherein the ad hoc query vector q is defined as being equal to $q^T P \Sigma^{-1}_k$.

8. A method of calculating similarity or substantial similarity between a first document $V_i$ and at least one other document $V_j$ representing a plurality of chemical and textual descriptors, comprising the steps of:
   (a) creating at least one chemical descriptor and at least one text descriptor for a plurality of compounds in each document;
   (b) preparing a descriptor template, wherein the descriptor template comprises:
      at least one text source containing textual and chemical descriptions, and;
      at least one descriptor associated with each respective text source,
      wherein the entries in the descriptor template indicate the the relevance of a descriptor with respect to a text source;
   (c) performing a decomposition operation on the descriptor template to produce result;
   (d) using the result to compute the similarity between the first document and the at least one other document; and
   e) outputting at least a subset of the at least one other document ranked in order of similarity to the first document.

9. The method as recited in claim 8, wherein said creating step includes generating atom pair and topological torsion descriptors from chemical connection tables of the collection of compounds.

10. The method as recited in claim 8, wherein said creating step includes creating an index of descriptors and an index of compounds in the collection.

11. The method as recited in claim 8 wherein said performing step comprises the step of:
   generating matrices P, $\Sigma$, and $Q^T$, such that descriptor matrix $X=P\Sigma Q^T$, wherein
      P is a mxr matrix, called the left singular matrix (r is the rank of X), and its columns are the eigenvectors of $XX^T$ corresponding to nonzero eigenvalues;
      Q is a nxr matrix, called the right singular matrix, whose columns are the eigenvectors of $X^TX$ corresponding to nonzero eigenvalues; and
      $\Sigma$ is a rxr diagonal matrix whose nonzero elements, $\sigma_1$, $\sigma_2$, ..., $\sigma_r$ called singular values, are the square roots of the eigenvalues and have the property that $\sigma_1 \geq \sigma_2 \geq ... \geq \sigma_r$.

12. The method as recited in claim 11 wherein said computing step comprises the step of computing the dot product between the $i^{th}$ and $j^{th}$ rows of the matrix $Q\Sigma$.

13. The method as recited in claim 8 wherein the first document is initially an ad hoc query vector q, further comprising the step of:
   determining a matrix $X_k$, wherein $X_k$ is the matrix of rank k which is equivalent to $P_k\Sigma_k Q^T_k$, and is the least squares closest to X; and
   projecting the ad hoc query vector onto $X_k$.

14. The method as recited in claim 13 wherein the ad hoc query vector q is defined as being equal to $q^T P \Sigma^{-1}_k$.

15. A method of calculating similarity or substantial similarity between a chemical descriptor $d_j$ and at least one document $V_i$ characterizing one or more of a plurality of chemical and textual descriptors, comprising the steps of:
   (a) creating at least one chemical descriptor and at least one text descriptor for a plurality of compounds in each document;
   (b) preparing a descriptor template, wherein the descriptor template comprises:

at least one text source containing textual and chemical descriptions, and;

at least one descriptor associated with each respective text source, wherein the entries in the descriptor template indicate the the relevance of a descriptor with respect to a text source;

(c) performing a decomposition operation of the descriptor template to produce a result;

(d) using the result to compute the similarity between at least one of the at least one document $V_i$ and the chemical descriptor $d_j$; and (e) outputting at least a subset of the at least one document ranked in order of similarity to the chemical descriptor.

16. The method as recited in claim 15, wherein said creating step includes generating atom pair and topological torsion descriptors from chemical connection tables of the collection of compounds.

17. The method as recited in claim 15, wherein said creating step includes creating an index of descriptors and an index of compounds in the collection.

18. The method as recited in claim 15 wherein said performing step comprises the step of:

generating matrices P, $\Sigma$, and $Q^T$, such that descriptor matrix $X=P\Sigma Q^T$, wherein P is a mxr matrix, called the left singular matrix (r is the rank of X), and its columns are the eigenvectors of $XX^T$ corresponding to nonzero eigenvalues;

Q is a nxr matrix, called the right singular matrix, whose columns are the eigenvectors of $X^TX$ corresponding to nonzero eigenvalues; and $\Sigma$ is a rxr diagonal matrix whose nonzero elements, $\sigma_1, \sigma_2, \ldots, \sigma_r$ called singular values, are the square roots of the eigenvalues and have the property that $\sigma_1 \geq \sigma_2 \geq \ldots \geq \sigma_r$.

19. The method as recited in claim 18 wherein said computing step comprises the step of computing the dot product between the $i^{th}$ row of the matrix $P\Sigma$ and the $j^{th}$ row of the matrix $Q\Sigma$.

20. The method as recited in claim 15 wherein the chemical descriptor is initially an ad hoc query vector q, further comprising the step of:

determining a matrix $X_k$, wherein $X_k$ is the matrix of rank k which is equivalent to $P_k\Sigma_kQ^T_k$, and is the least squares closest to X; and projecting the ad hoc query vector onto $X_k$.

21. The method as recited in claim 20 wherein the ad hoc query vector q is defined as being equal to $q^TP\Sigma^{-1}_k$.

22. A method of calculating similarity or substantial similarity between a textual descriptor $d_j$ and at least one document $V_i$ characterizing a plurality of chemical and textual descriptors, comprising the steps of:

(a) creating at least one chemical descriptor and at least one textual descriptor for a plurality of compounds in each document;

(b) preparing a descriptor, wherein the descriptor comprises:
at least one text source containing textual and chemical descriptions, and;
at least one descriptor associated with each respective text source,
wherein the entries in the descriptor indicate the the relevancy of a descriptor with respect to a text source;

(c) performing an operation on the descriptor matrix to produce at least one result;

(d) using the at least one result to determine the similarity between at least one of the at least one document $V_i$ and textual descriptor $d_j$; and (e) outputting at least a subset of the at least one document with respect to the similarity to the chemical descriptor.

23. The method as recited in claim 22, wherein said creating step includes generating atom pair and topological torsion descriptors from chemical connection tables of the collection of compounds.

24. The method as recited in claim 22, wherein said creating step includes creating an index of descriptors and an index of compounds in the collection.

25. The method as recited in claim 22 wherein said performing step comprises the step of:

generating matrices P, $\Sigma$, and $Q^T$, such that descriptor matrix $X=P\Sigma Q^T$, wherein P is a mxr matrix, called the left singular matrix (r is the rank of X), and its columns are the eigenvectors of $XX^T$ corresponding to nonzero eigenvalues;

Q is a nxr matrix, called the right singular matrix, whose columns are the eigenvectors of $X^TX$ corresponding to nonzero eigenvalues; and $\Sigma$ is a rxr diagonal matrix whose nonzero elements, $\sigma_1, \sigma_2, \ldots, \sigma_r$ called singular values, are the square roots of the eigenvalues and have the property that $\sigma_1 \geq \sigma_2 \geq \ldots \geq \sigma_r$.

26. The method as recited in claim 25 wherein said computing step comprises the step of computing the dot product between the $i^{th}$ row of the matrix $P\Sigma$ and the $j^{th}$ row of the matrix $Q\Sigma$.

27. The method as recited in claim 22 wherein the textual descriptor $d_j$ is initially an ad hoc query vector q, further comprising the step of:

determining a matrix $X_k$, wherein $X_k$ is the matrix of rank k which is equivalent to $P_k\Sigma_kQ^T_k$, and is the least squares closest to X; and projecting the ad hoc query vector onto $X_k$.

28. The method as recited in claim 27 wherein the ad hoc query vector q is defined as being equal to $q^TP\Sigma^{-1}_k$.

29. A computer readable medium including instructions being executable by a computer, the instructions instructing the computer to generate a searchable representation of chemical structures, the instructions comprising:

(a) creating at least one chemical descriptor and at least one text descriptor for each compound in a collection of compounds;

(b) preparing a descriptor, wherein the descriptor comprises
at least one text source containing textual and chemical descriptions, and;
at least one descriptor associated with each respective text source,
wherein the entries in the descriptor indicate the relevancy of a descriptor with respect to a text source;

(c) performing an operation on the descriptor to produce at least one result;

(d) using the at least one result to determine the similarity between the first chemical descriptor $d_i$ and the at least one other chemical descriptor $d_j$; and (e) outputting at least a subset of the at least one other chemical descriptor with respect to the similarity to the first chemical descriptor.

30. The computer readable medium as recited in claim 29 wherein said creating step includes generating atom pair and topological torsion descriptors from chemical connection tables of the collection of compounds.

31. The computer readable medium as recited in claim 29 wherein said creating step includes creating an index of descriptors and an index of compounds in the collection.

32. The computer readable medium as recited in claim 29 wherein said performing step comprises the step of:

generating matrices P, Σ, and $Q^T$, such that descriptor matrix $X = P\Sigma Q^T$, wherein:

P is a mxr matrix, called the left singular matrix (r is the rank of X), and its columns are the eigenvectors of $XX^T$ corresponding to nonzero eigenvalues;

Q is a nxr matrix, called the right singular matrix, whose columns are the eigenvectors of $X^T X$ corresponding to nonzero eigenvalues; and Σ is a rxr diagonal matrix whose nonzero elements, $\sigma_1, \sigma_2, \ldots, \sigma_r$ called singular values, are the square roots of the eigenvalues and have the property that $\sigma_1 \geq \sigma_2 \geq \ldots \geq \sigma_r$.

33. The computer readable medium as recited in claim 32 wherein said computing step comprises the step of computing the dot product between the $i^{th}$ and $j^{th}$ rows of the matrix PΣ.

34. The computer readable medium as recited in claim 29 wherein the first chemical descriptor is initially an ad hoc query vector q, further comprising the step of:

determining a matrix $X_k$, wherein $X_k$ is the matrix of rank k which is equivalent to $P_k \Sigma_k Q^T_k$, and is the least squares closest to X; and projecting the ad hoc query vector onto $X_k$.

35. The computer readable medium as recited in claim 34 wherein the ad hoc query vector q is defined as being equal to $q^T P\Sigma hu -1_k$.

36. A computer readable medium for calculating the similarity between a first text source and at least one other text source from a plurality of chemical and textual descriptors, comprising the steps of:

(a) creating at least one chemical descriptor and at least one text descriptor for each compound in each text source;

(b) preparing a descriptor, wherein the descriptor comprises:
at least one text source containing textual and chemical descriptions, and;
at least one descriptor associated with each respective text source,
wherein the descriptor indicates the relevance of a corresponding descriptor with respect to a text source;

(c) performing an operation on the descriptor to produce at least one result;

(d) using the at least one result to determine the similarity between the first text source $V_i$ and the at least one other text source $V_j$; and e) outputting at least a subset of the at least one other test source with respect to the similarity to the first text source.

37. The computer readable medium as recited in claim 36, wherein said creating step includes generating atom pair and topological torsion descriptors from chemical connection tables of the collection of compounds.

38. The computer readable medium as recited in claim 36, wherein said creating step includes creating an index of descriptors and an index of compounds in the collection.

39. The computer readable medium as recited in claim 36 wherein said performing step comprises the step of:

generating matrices P, Σ, and $Q^T$, such that descriptor matrix $X = P\Sigma Q^T$, wherein P is a mxr matrix, called the left singular matrix (r is the rank of X), and its columns are the eigenvectors of $XX^T$ corresponding to nonzero eigenvalues;

Q is a nxr matrix, called the right singular matrix, whose columns are the eigenvectors of $X^T X$ corresponding to nonzero eigenvalues; and Σ is a rxr diagonal matrix whose nonzero elements, $\sigma_1, \sigma_2, \ldots, \sigma_r$ called singular values, are the square roots of the eigenvalues and have the property that $\sigma_1 \geq \sigma_2 \geq \ldots \geq \sigma_r$.

40. The computer readable medium as recited in claim 39 wherein said computing step comprises the step of computing the dot product between the $i^{th}$ and $j^{th}$ rows of the matrix QΣ.

41. The computer readable medium as recited in claim 36 wherein the first document is initially an ad hoc query vector q, further comprising the step of:

determining a matrix $X_k$, wherein $X_k$ is the matrix of rank k which is equivalent to $P_k \Sigma_k Q^T_k$, and is the least squares closest to X; and projecting the ad hoc query vector onto $X_k$.

42. The computer readable medium as recited in claim 41 wherein the ad hoc query vector q is defined as being equal to $q^T P\Sigma^1_k$.

43. A computer readable medium for determining the similarity between a chemical descriptor $d_j$ and at least one text source $V_i$ from a plurality of chemical and textual descriptors, comprising the steps of:

(a) creating at least one chemical descriptor and at least one text descriptor for each compound in each text source;

(b) preparing a descriptor, wherein the descriptor comprises:
at least one text source containing textual and chemical descriptions, and;
at least one descriptor associated with each respective text source,
wherein the entries in the descriptor indicate the relevance of a corresponding descriptor with respect to a text source;

(c) processing the descriptor to produce at least one result;

(d) using the at least one result to determine the similarity between at least one of the at least one text source $V_i$ and the chemical descriptor $d_j$; and e) outputting at least a subset of the at least one text source with respect to the similarity to the chemical descriptor.

44. The computer readable medium as recited in claim 43, wherein said creating step includes generating atom pair and topological torsion descriptors from chemical connection tables of the collection of compounds.

45. The computer readable medium as recited in claim 43, wherein said creating step includes creating an index of descriptors and an index of compounds in the collection.

46. The computer readable medium as recited in claim 43 wherein said performing step comprises the step of:

generating matrices P, Σ, and $Q^T$, such that descriptor matrix $X = P\Sigma Q^T$, wherein P is a mxr matrix, called the left singular matrix (r is the rank of X), and its columns are the eigenvectors of $XX^T$ corresponding to nonzero eigenvalues;

Q is a nxr matrix, called the right singular matrix, whose columns are the eigenvectors of $X^T X$ corresponding to nonzero eigenvalues; and Σ is a rxr diagonal matrix whose nonzero elements, $\sigma_1, \sigma_2, \ldots, \sigma_r$ called singular values, are the square roots of the eigenvalues and have the property that $\sigma_1 \geq \sigma_2 \geq \ldots \geq \sigma_r$.

47. The computer readable medium as recited in claim 46 wherein said computing step comprises the step of computing the dot product between the $i^{th}$ row of the matrix $P\Sigma$ and the $j^{th}$ row of the matrix $Q\Sigma$.

48. The computer readable medium as recited in claim 43 wherein the chemical descriptor is initially an ad hoc query vector q, further comprising the step of:

determining a matrix $X_k$, wherein $X_k$ is the matrix of rank k which is equivalent to $P_k\Sigma_k Q^T_k$, and is the least squares closest to X; and projecting the ad hoc query vector onto $X_k$.

49. The computer readable medium as recited in claim 48 wherein the ad hoc query vector q is defined as being equal to $q^T P \Sigma^1_k$.

50. A computer readable medium for determining the similarity between at least one textual descriptor $d_j$ and at least one text source $V_i$ from a plurality of chemical and textual descriptors, comprising the steps of:

(a) creating at least one chemical descriptor and at least one textual descriptor for each compound in each text source;

(b) preparing a descriptor, wherein the descriptor comprises at least one text source containing textual and chemical descriptions, and;

at least one descriptor associated with each respective text source, wherein the entries in the descriptor indicate the relevance of a corresponding descriptor with respect to a text source;

(c) processing the descriptor to produce at least one result;

(d) using the at least one result to determine the similarity between at least one of the at least one text source $V_i$ and at least one textual descriptor $d_j$ and e) outputting at least a subset of the at least one text source with respect to similarity to at least one of the chemical and textual descriptors.

51. The computer readable medium as recited in claim 50, wherein said creating step includes generating atom pair and topological torsion descriptors from chemical connection tables of the collection of compounds.

52. The computer readable medium as recited in claim 50, wherein said creating step includes creating an index of descriptors and an index of compounds in the collection.

53. The computer readable medium as recited in claim 50 wherein said performing step comprises the step of:

generating matrices P, $\Sigma$, and $Q^T$, such that descriptor matrix $X = P\Sigma Q^T$, wherein P is a mxr matrix, called the left singular matrix (r is the rank of X), and its columns are the eigenvectors of $XX^T$ corresponding to nonzero eigenvalues;

Q is a nxr matrix, called the right singular matrix, whose columns are the eigenvectors of $X^T X$ corresponding to nonzero eigenvalues; and $\Sigma$ is a rxr diagonal matrix whose nonzero elements, $\sigma_1$, $\sigma_2$, ..., $\sigma_r$ called singular values, are the square roots of the eigenvalues and have the property that $\sigma_1 \geq \sigma_2 \geq ... \geq \sigma_r$.

54. The computer readable medium as recited in claim 53 wherein said computing step comprises the step of computing the dot product between the $i^{th}$ row of the matrix $P\Sigma$ and the $j^{th}$ row of the matrix $Q\Sigma$.

55. The computer readable medium as recited in claim 50 wherein the textual descriptor $d_j$ is initially an ad hoc query vector q, further comprising the step of:

determining a matrix $X_k$, wherein $X_k$ is the matrix of rank k which is equivalent to $P_k\Sigma_k Q^T_k$, and is the least squares closest to X; and projecting the ad hoc query vector onto $X_k$.

56. The computer readable medium as recited in claim 55 wherein the ad hoc query vector q is defined as being equal to $q^T P \Sigma^1_k$.

57. A method of calculating similarity or substantial similarity between a first chemical descriptor and at least one other chemical descriptor from a plurality of chemical and textual descriptors, comprising the steps of:

(a) creating at least one chemical descriptor and at least one textual descriptor for at least one compound in a collection of compounds;

(b) preparing a similarity descriptor wherein the similarity descriptor characterizes at least two text sources containing textual and chemical descriptions and indicates the frequency of the descriptions;

(c) processing the similarity descriptor to produce at least one result;

(d) using at least a portion of the at least one result to determine the similarity between the first chemical descriptor $d_i$ and at least one other chemical descriptor $d_j$; and e) outputting at least a subset of the at least one other chemical descriptor with respect to similarity to the first chemical descriptor.

58. A method of calculating similarity or substantial similarity between a first chemical descriptor and at least one other chemical descriptor from a plurality of chemical and textual descriptors, comprising the steps of:

(a) creating at least one chemical descriptor and at least one textual descriptor for at least a plurality compounds in a collection of compounds;

(b) preparing a frequency descriptor, from two or more independent source documents, indicating the frequency of the textual and chemical descriptors within each document for the plurality of compounds (c) processing the frequency descriptor to produce at least one result;

(d) using at least a portion of the at least one result to determine the similarity between the first chemical descriptor and at least one of the other chemical descriptor; and e) outputting at least a subset of the at least one other chemical descriptor with respect to the similarity to the first chemical descriptor.

59. A method of calculating similarity or substantial similarity between a first chemical descriptor and at least one other chemical descriptor from a plurality of chemical and textual descriptors, comprising the steps of:

(a) determining the similarity between the first chemical descriptor and at least one of the other chemical descriptors using a at least two independent text sources each containing a known number of one or more occurrences of at least one textual descriptor and at least one of the other chemical descriptors; and (b) outputting at least a subset of the similarity or substantial similarity of the first chemical descriptor with respect to the other chemical descriptors.

60. A method of calculating similarity or substantial similarity between a first chemical descriptor, $d_i$, and a second chemical descriptor, $d_j$, associated with one or more compounds, comprising the steps of:

(a) preparing a descriptor matrix X, wherein the descriptor matrix comprises a frequency of each of one or more chemical descriptors and one or more text descriptors in each of two or more source documents;

(b) performing a decomposition operation on the descriptor matrix to produce at least a left singular matrix;

(c) computing a rank of matrix X that is the least squares closest; and (d) computing the dot product between the ith and jth rows, corresponding to the first and second chemical descriptors, respectively, of the left singular matrix, over the least squares rank.

61. The method according to claim 60, further comprising the step of outputting the dot product.

62. A method of calculating similarity or substantial similarity between a first chemical descriptor and at least one other chemical descriptor from a plurality of chemical and textual descriptors, comprising the steps of:

(a) creating at least one chemical descriptor and at least one textual descriptor for at least one compound in a collection of compounds;

(b) preparing a similarity descriptor, wherein the similarity descriptor comprises:
a text source containing textual and chemical descriptions, and;
a descriptor associated with each respective text source, wherein the similarity descriptor indicates the relevancy of a descriptor with respect to a text source;

(c) processing the similarity descriptor to produce at least one result;

(d) using the at least one result to determine the similarity between at least one of the first chemical descriptor $d_i$ and the text source with the at least one other chemical descriptor $d_j$; and e) outputting at least a subset of the at least one other chemical descriptor with respect to similarity to at least one of the first chemical descriptor and the text source.

63. A method of calculating similarity or substantial similarity between a first chemical descriptor and at least one other chemical descriptor from a plurality of chemical and textual descriptors, comprising the steps of:

(a) creating at least one chemical descriptor and at least one textual descriptor for at least one of the compounds in a collection of compounds;

(b) preparing a similarity descriptor, wherein the similarity descriptor comprises:
a text source containing the at least one textual and chemical descriptors, and
a corresponding descriptor associated with and having a predetermined relevancy with respect to the text source;

(c) processing the similarity descriptor to produce at least one result;

(d) using the at least one result to determine the similarity between the first chemical descriptor and at least one of the other chemical descriptor and the text source; and e) outputting at least a subset of the at least one other chemical descriptor with respect to the similarity to at least one of the first chemical descriptor and the text source.

64. A method of calculating similarity or substantial similarity between a first chemical descriptor and at least one other chemical descriptor from a plurality of chemical and textual descriptors for at least one compound in a collection of compounds, comprising the steps of:

(a) determining the similarity between the first chemical descriptor and at least one of the other chemical descriptor and the text source using a similarity descriptor comprising a text source containing the at least one textual and chemical descriptors, and a corresponding descriptor associated with and having a predetermined relevancy with respect to the text source; and (b) outputting at least a subset of the at least one other chemical descriptor with respect to the similarity to at least one of the first chemical descriptor and the text source.

\* \* \* \* \*